United States Patent [19]

Stauffer

[11] 4,312,493

[45] Jan. 26, 1982

[54] APPARATUS FOR CONTROLLED LIQUID ADMINISTRATION

[76] Inventor: Rita A. Stauffer, 1016 W. Hollywood St., Chicago, Ill. 60660

[21] Appl. No.: 178,934

[22] Filed: Aug. 18, 1980

Related U.S. Application Data

[63] Continuation-in-part of Ser. No. 38,000, May 5, 1979, abandoned, which is a continuation-in-part of Ser. No. 801,810, May 31, 1977.

[51] Int. Cl.³ .......................... F16K 7/06; A61M 5/00
[52] U.S. Cl. .................................... 251/8; 128/214 R
[58] Field of Search ............ 128/214 R, 214 C, 214.2, 128/227, 274; 251/4, 7–10; 222/207, 527, 530; 119/14.51

[56] References Cited

U.S. PATENT DOCUMENTS

| | | | |
|---|---|---|---|
| 1,723,066 | 8/1929 | Ogden | 251/215 |
| 2,640,675 | 6/1953 | Farris | 251/8 |
| 3,048,171 | 8/1962 | Grau | 128/214.2 |
| 3,079,891 | 2/1963 | Rodgers | 138/118 |
| 3,476,111 | 11/1969 | Matheson | 128/227 |
| 3,507,278 | 4/1970 | Werding | 128/214 F |
| 3,543,753 | 12/1970 | Weinstein | 128/214 F |
| 3,941,126 | 3/1976 | Dietrich et al. | 128/214 R |
| 4,172,580 | 10/1979 | Raftis et al. | 251/8 |

FOREIGN PATENT DOCUMENTS 535034 10/1955 Italy ........................................ 251/8

*Primary Examiner*—Dalton L. Truluck
*Attorney, Agent, or Firm*—McWilliams, Mann & Zummer

[57] ABSTRACT

A control apparatus for a parenteral administration set which includes a calibrated rate control clamp for determining the time period over which the contents of a standard supply container of physiological liquid is delivered. The clamp selectively constricts the tubing interconnecting the supply container with a patient and the constriction is correlated with a calibrated scale. A spring device is provided to assure that the constriction is removed responsive to loosening of the clamp. This provides for an easy and rapid setting of a given time period over which the known volume of the liquid in the supply container is infused into the patient.

3 Claims, 8 Drawing Figures

U.S. Patent   Jan. 26, 1982   Sheet 1 of 2   4,312,493
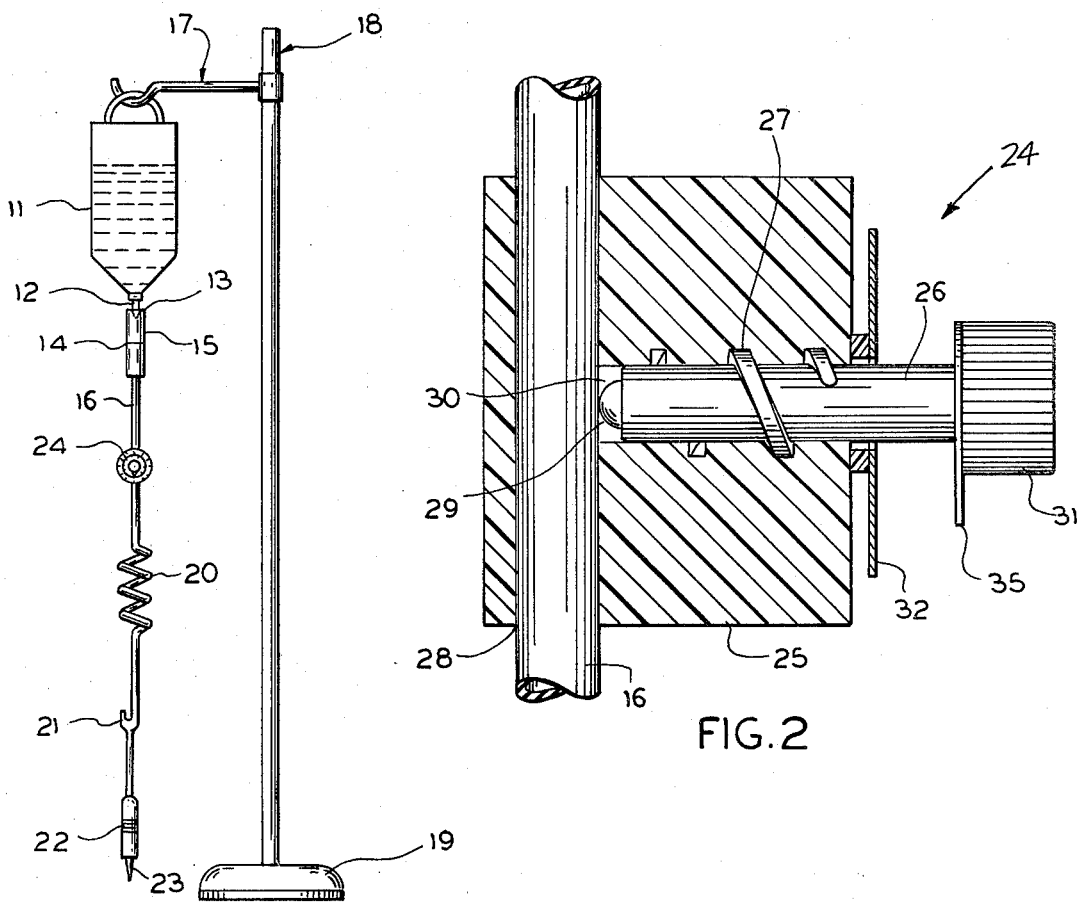
FIG.1
FIG.2
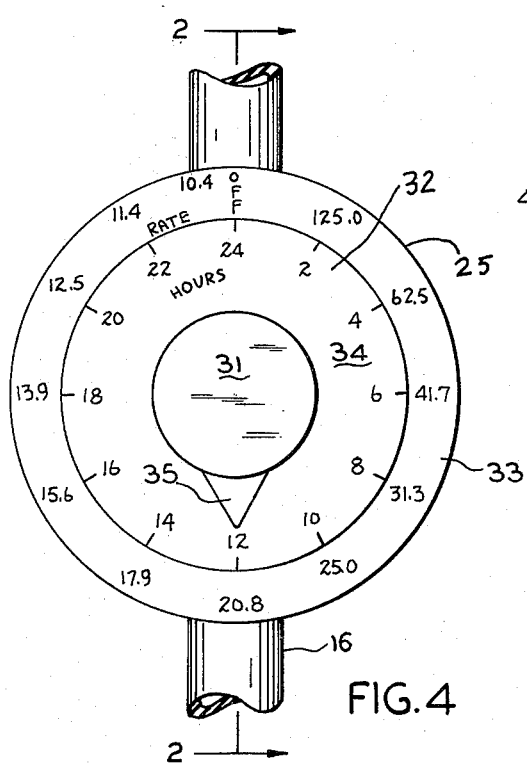
FIG.4
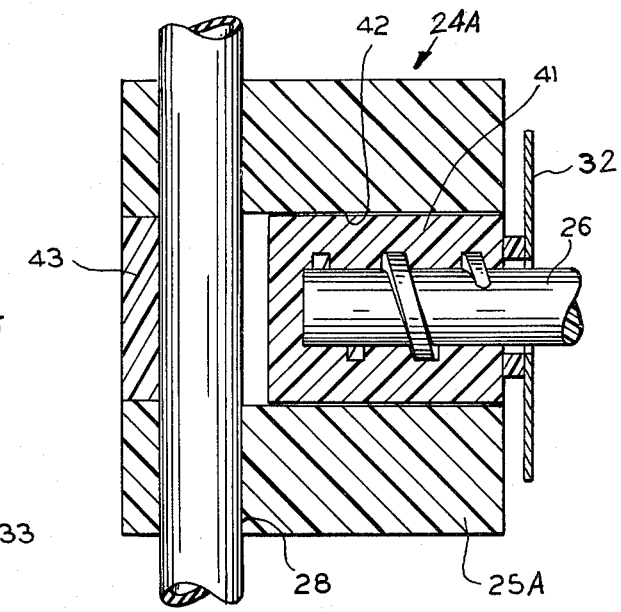
FIG.3

APPARATUS FOR CONTROLLED LIQUID ADMINISTRATION

This application is a continuation-in-part of my application Ser. No. 038,000, filed May 5, 1979, which is a substitute for my abandoned application Ser. No. 850,947, filed Nov. 14, 1977, which was a continuation-in-part of my abandoned application Ser. No. 801,810, filed on May 31, 1977.

This invention relates to an apparatus for regulating the administration of fluids, and more particularly, relates to an improved rate control apparatus in which the rate of flow is correlated with a calibrated scale.

Parenteral solutions such as intravenous feeding solutions are normally transferred from a container to a patient by means of parenteral administration sets. The transfer of the physiological liquid from the container and subsequent infusion into the patient is achieved by suspending the container; e.g., a glass or plastic bottle or flexible bag, above the patient. The insertion means of the parenteral administration set, which is inserted into the supply container of liquid, is connected in series with a drip chamber, tubing and a means for attaching a needle.

In the prior art, roller clamps for controlling the flow rate of liquid are attached to the tubing. After appropriate steps to remove trapped air from the administration set and establish a drip rate, the needle is inserted into the patient.

One major disadvantage of the aforementioned administration sets are the roller clamps which are attached to the tubing in order to control the drip rate. The roller clamps comprise an inclined plane, a circular roller containing ridges and means for guiding the roller and tubing. The tubing is positioned between the inclined plane and the roller. By adjusting the position of the roller along the inclined plane, the tubing is compressed thereby reducing the rate of flow of liquid through the constriction. In order to achieve a given drip rate, the operator must selectively move the roller and determine the drip rate by counting the drips, mentally convert the drops into milliliters, adjust the position of the roller, and repeat the above sequence until the desired drip rate is achieved.

This means of controlling the drip rate is both cumbersome and further, suffers from the disadvantage that the roller clamp can slip during the infusion process thereby altering the drip rate. The consequences of such a slippage can be very serious, particularly, if medication is being administered to the patient. The drip rate must, therefore, be periodically monitored and adjusted, if necessary.

Various solutions for measuring both the rate and volume of delivery have been proposed. U.S. Pat. No. 3,776,229 discloses an apparatus for measuring these quantities. A valve structure is employed which permits the determination of the rate and volume of delivery. The actual drip rate of the fluid infused into the patient is, however, controlled by a conventional roller clamp which requires counting of changes to establish a given drip rate.

Other liquid administration sets for delivering a predetermined volume of liquid are described in U.S. Pat. Nos. 3,774,603; 3,844,283 and 3,625,211. These administration sets also employ a conventional clamp for controlling the flow rate. They further require secondary chambers and valve means.

A problem encountered when using constriction means for constricting the tube to control the fluid flow rate is that the plastic tube as a "memory" and therefore remains constricted, even after removal of the constriction means. Hence, it is difficult and often impossible to effectively go from a slow rate to a faster rate.

If very accurate and constant drip rates are desired, U.S. Pat. No. 3,931,818 discloses a sump interconnected to a flow controlling float chamber by means of a double bore metering tube. It is also possible to regulate the drip rate electronically as disclosed in U.S. Pat. No. 3,871,229. The constriction means for controlling the rate of flow as described in this patent is a threaded shaft which constricts a tube carrying the fluid. While the drip rate can be controlled manually, the sensing of the drip rate is electronic and thus the rate of flow, as measured by the drops per minute scale, is determined electronically.

These complicated means for controlling the drip rate are economically impractical for use in the usual parenteral administration set, since such sets are designed for one-time use and are disposable.

The present invention relates to a parenteral administration set for infusing clear liquids, such as a glucose feeding solution, from a supply container into a patient. An important feature of the administration set relates to a clamp for restricting the flow of liquid through flexible tubing which connects a supply container to a patient. The clamp includes a threaded shaft by which means the constriction on the tubing can be varied and a calibrated scale which cooperates with the threaded shaft, whereby an operator can quickly set the clamp for a predetermined time period and drip rate in which the contents of a supply container can be infused into the patient.

A substantial majority of intravenous feedings involve five (5%) percent by weight glucose solutions in a 1000 ml container. The clamp, in a preferred embodiment is, therefore, calibrated against such a solution suspended at a standard height of five feet. By using the time scale on the clamp, an operator can quickly select the time period over which the contents of the 1000 ml container are delivered. Alternatively, the drip rate scale may be used to select a predetermined drip rate and the amount of liquid delivered over any given period can be quickly calculated.

It is therefore, an object of the present invention to provide calibrated apparatus for delivering the contents of containers holding fluid for intravenous injection.

Another object of the present invention is to provide calibrated apparatus for quickly and accurately setting a given time period over which the contents of a standard supply container will be delivered.

A related object of the present invention is to provide calibrated clamps for selectively constricting the tubing used in delivering the intravenous fluid.

Still another object of the present invention is to provide resilient means for assuring that the constriction of the tubing is removed and the clamp is loosened.

Another object of this invention is to provide calibrated apparatus for quickly and accurately setting given drip rates.

Another object is to provide simply drip rate controlling apparatus which can be economically manufactured for use in disposable parenteral administration sets.

These and other objects of the present invention will be described more fully in the following detailed description of the invention.

FIG. 1 is an elevational view of the administration apparatus including a clamp embodying the subject invention;

FIG. 2 is a sectional view of a preferred embodiment of the clamp, showing the rate controlling mechanism;

FIG. 3 is a sectional view of another preferred embodiment of the clamp with rate controlling mechanisms;

FIG. 4 is a partial top view of the clamp, showing the calibrated scale;

Figure 6:
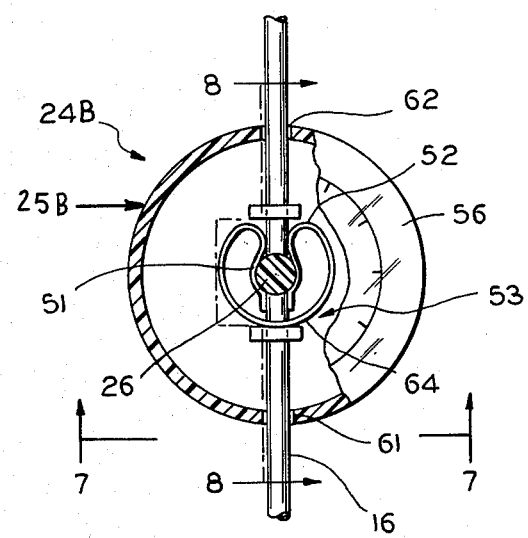
FIG. 6 is a partial sectional plan view of the clamp showing a tube diameter restoring device.
Figure 5:
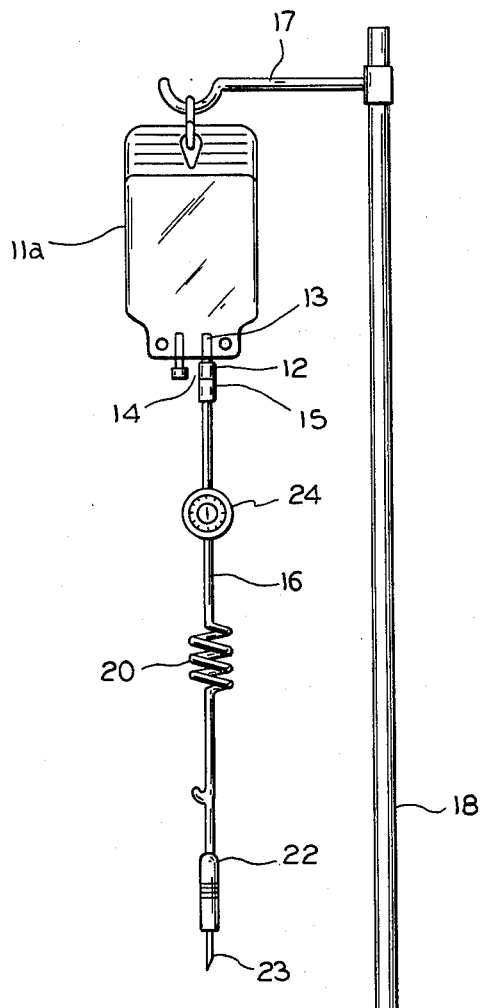
FIG. 5 is an elevational view of the administration apparatus, as shown in FIG. 1, but with a plastic bag supply container in place of the bottle.

FIG. 1 discloses an administration set for infusing a clear intravenous feeding solution into a patient. A supply container, which may be the bottle 11 shown in FIG. 1 or the plastic container 11 shown in FIG. 6, is suspended from a headstand which comprises a base 19, supporting column 18 and hook 17 attached to said headstand at a standard height of five feet. The administration set includes flexible tubing 16 attached to a flexible drip chamber 15. The drip chamber contains an infiltration indicator 14 and is connected to a drop cannula 13 and an insertion spike 12. The flexible tubing 16 is shown containing a coil 20, an insertion site 21, and is attached to a latex sleeve 22 which contains a rigid needle adapter 23. Attached to the tubing is a clamp or pinch valve 24 for controlling the flow of liquid through the tubing. The coil 20 is resilient and resumes the coiled shape after being stretched, similar to the familiar coiled telephone cords.

Having described the basic components of the parenteral administration set, the details of the clamp or pinch valve 24 will be discussed. As shown in FIG. 2, the clamp comprises a solid base structure or body 25 which is preferably made of a molded plastic material. In the lower portion of the base structure is a hole or through opening or passage 28 which traverses the length of the base, the hole 28 being of sufficient diameter to accommodate the flexible tubing 16 in slidable close fitting relation. A threaded rotatable shaft 26, having a rounded end 29, extends through threaded hole 27 from the top of the base structure to the lower portion containing the tubing 16. The rounded end 29 passes through an opening 30 which enables contact of the shaft 26 with the tubing 16 so that it can be pinched against the portion of body 25 opposing shaft 26, on the opposite side of passage 28, which body portion serves as the valve seat.

Mounted on the shaft 26 are a knurled indicator knob 31 and a calibrated scale plate 32. The pitch of the threads 27 is such that one full revolution of shaft 26 will cause movement of the shaft 26 in an upward or downward direction by approximately the diameter of the tubing 16. The upward or downward movement of the shaft 26 per increment of rotation of knob 31 is a function of the pitch of threaded shaft 26.

In FIG. 3 the clamp 24A is shown as comprising a solid body 25A having a hole 28 traversing the length of its base. The flexible tubing 16 is accommodated in hole 28. Rotating indicator knob 31 causes rotation of threaded shaft 26 which in turn moves hammer 41 which is threadably coupled to the shaft 26 to move in hole 42 in the body 25A. The hammer 41 presses the tubing 16 against anvil 43, that serves as the valve seat in the embodiments to constrict the tubing 16 a controlled amount.

The scale side view of the clamp is shown in FIG. 4. The calibrated scale plate 32 is attached to shaft 26. A pointer 35 is attached to the base of knurled knob 31. The scale 34 of scale plate 32 is calibrated in hours required to deliver the contents of a 1000 ml supply container hung at a height of five feet and containing, for example a five (5%) percent glucose solution. The corresponding drip rate in drops per minute for the respective time periods is shown on scale 33 formed on body 25A.

To explain how the administration set is operated, reference is made to the Figures. The pointer 35 of the indicator knob 31 is rotated to the "off" position, as shown on scale 33. In the "off" position, the tubing 16 is completely closed due to pressure exerted by shaft end 29 or hammer 41. The protective disc is removed from supply container 11 and the protective cap is removed from the insert spike 12. The flexible drip chamber 15 is squeezed, and the insertion spike 12 then is hung from hook 17 at a height of five feet. The drip chamber is then filled to the infiltration indicator mark 14 by alternately squeezing and releasing the drip chamber. In order to clear the tubing of air, the indicator knob 31 is rotated to an "on" position and the tubing completely filled with liquid.

At this point, the operator can select a point on the hourly scale 34. The indicator knob 31 is simply rotated until the desired hourly setting is indicated by the "off" marker of scale 33. This corresponds to the number of hours required to deliver, for example, 1000 ml of five (5%) percent glucose solution contained in the supply container. If a 500 ml container is employed, the hourly scale 34 will be divided by a factor of 2.

Alternatively, the operator may use the drip rate scale 33, which is calibrated in drops per minute, and moving knob 31 to set pointer 35 at the desired drip rate of scale 33. The rate of discharge of solution from the drip chamber 15 is controlled by the pressure on tubing 16 which is created by movable shaft 26 of clamp 24. Of course, the rate of discharge of solution from the drip chamber also controls the drip rate from the drop cannula 13. Any given drive rate may be selected from the calibrated drip rate scale 33 and the volume delivered over any given time period quickly calculated.

Figures 7, 8:
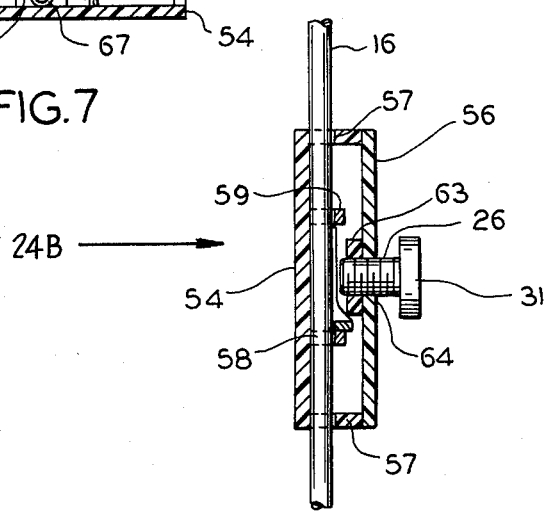
FIG. 7 is a partial sectional view of the clamp of FIG. 6 looking in the direction of the arrows 7—7.
FIG. 8 is a sectional view of the clamp of FIG. 6 looking in the direction of the arrows 8—8.

Another preferred embodiment 24B of the clamp 24 is shown in FIGS. 6–8. Therein means are provided for assuring that the constricted tube 16 follows the shaft of the clamping device as the indicator knob is rotated from the "off" to the "on" position.

More particularly, as shown in FIGS. 6–8, resilient means such as spring arms 51 and 52 of shaped spring 53 normally apply pressure to opposite sides of tubing 16. The pressure is applied in the quadrants removed 90 degrees from the point of pressure application applied by the screw shaft 26.

The embodiment of the clamp means 24B shown in FIGS. 6, 7 and 8 is comprised of a body 25B in the form of a bottom disk 54 spaced apart from a top disk 56 by a center cylindrical section 57. Preferably, the top and bottom disks are joined together using well known adhesives. The disks 54 and 56 and cylindrical section 57 are constructed of a suitable plastic, such as plexiglass or Bakelite.

Means, such as apertured tabs or panels 58 and 59, are provided for positioning and retaining the tube 16 aligned with the shaft 26. A pair of oppositely disposed apertures 61 and 62 are provided in center section 57 to enable the tube 16 to pass through clamp 24B. The apertures of panels 58 and 59 form, with apertures 61 and 62 of section 57, the through opening or passage through which tube 16 is to extend through body 25B. A threaded stabilizing section 63 is provided underneath centrally located threaded hole 64 in a top disk 56 to stabilize shaft 26 of clamp 24B. The spring 53, as best seen in FIG. 6, may be characterized as a C-shaped clamp spring. The arms 51 and 52 are themselves shaped to fit around screw shaft 26 and nonetheless apply pressure to the sides of tubing 16 on both sides of the shaft 26, independent of the degree of clamping of shaft 26 against tubing 16. The base 64 of the C-shaped clamp spring 53 has a protuberance portion 66 rising from the arms thereof at the center of the ring shaped portion 66. A passage aperture 67 is provided through spring base 64 to enable the passage therethrough of tubing 16.

Since the present invention is subject to many changes and modifications in detail, all matter described hereinbefore or shown in the accompanying drawings is to be interpreted as illustrative and not as limiting.

I claim:

1. In a clamp valve device for controlling the flow of liquid through a flexible tube and including a body formed to define a through passage through which the tube is to extend when the valve device is appied thereto, a clamping member threadedly mounted in said body on one side of said passage intermediate the ends of said passage and extending normally thereof and movable, along an axis extending normally of said passage, toward the tube, when in the passage, to engage a side portion of the tube for constricting the tube, and away from the tube for releasing the tube, and a valve seat aligned with said axis and opposing said clamping member across the through passage against which the clamping member when rotated in its clamping direction compresses the tube to constrict the bore of same for controlling the flow of liquid therethrough, the improvement wherein:

said body defines a chamber about said axis adjacent the valve seat that is intersected by the through passage, and including a C-shaped clamping spring disposed in said chamber in a plane that is normal to said axis and extends longitudinally of said passage, said spring being substantially centered on said axis, said spring defining a bight portion that is apertured in alignment with said passage, to receive said tube on one side of said axis, and a pair of opposed end portions on the other side of said axis each including an extension that extends toward said bight portion adjacent its said aperture, said spring being formed to spring bias said extensions toward each other to clampingly receive the tube therebetween when the tube is disposed in the passage, said spring extensions being disposed to respectively compressively engage opposed side portions of the tube, when the tube is received in the passage, which side portions are to either side of the tube first mentioned side portion, circumferentially of the tube, for biasing the tube within said chamber such that the tube first mentioned side portion follows said clamping member to return the tube to open position when said clamping member is rotated to reduce constriction thereof.

2. The improvement set forth in claim 1 wherein:

said spring extensions are respectively shaped to receive said clamping member therebetween as it is moved to clamp the tube, when received in the passage, against the valve seat, while maintaining their said bias on the tube opposed side portions.

3. The improvement set forth in claim 1 wherein:

said chamber substantially exceeds the size of said spring in said plane, about said axis, and wherein said body includes a pair of spaced apart tabs disposed on either side of said axis that are aligned with, and are respectively formed with openings to in part define, the body passage, said spring being received between said tabs in close fitting relation thereto.

* * * * *